United States Patent
Chung et al.

(10) Patent No.: US 7,223,582 B2
(45) Date of Patent: May 29, 2007

(54) ESTERASE, ITS DNA, ITS OVEREXPRESSION AND PRODUCTION OF OPTICALLY ACTIVE ARYL PROPIONIC ACIDS USING THE SAME

(75) Inventors: Bong Hyun Chung, Daejeon (KR); Eun Gyo Lee, Daejeon (KR); Moon Sun Hahm, Daejeon (KR); Yeon Woo Ryu, Seoul (KR); Han Seung Lee, Daejeon (KR)

(73) Assignee: Korea Research Institute of BioScience and Biotechnology (KR)

( * ) Notice: Subject to any disclaimer, the term of this patent is extended or adjusted under 35 U.S.C. 154(b) by 408 days.

(21) Appl. No.: 10/859,572

(22) Filed: Jun. 3, 2004

(65) Prior Publication Data
US 2004/0219594 A1    Nov. 4, 2004

Related U.S. Application Data

(63) Continuation-in-part of application No. 10/118,047, filed on Apr. 9, 2002, now abandoned.

(30) Foreign Application Priority Data
Jan. 17, 2002 (KR) .......................... 2002-0002809

(51) Int. Cl.
C07H 21/04 (2006.01)
C12N 9/16 (2006.01)
C12N 1/20 (2006.01)
C12N 15/00 (2006.01)

(52) U.S. Cl. .................. 435/196; 536/23.2; 536/23.1; 435/197; 435/252.33; 435/320.1

(58) Field of Classification Search ................. None
See application file for complete search history.

(56) References Cited

U.S. PATENT DOCUMENTS 5,516,690 A    5/1996   Evans et al. ................ 435/280

(Continued)

FOREIGN PATENT DOCUMENTS

KR    1996-0014399    5/1996

(Continued)

OTHER PUBLICATIONS

Jones, et al., The cold-shock response—a hot topic, Molecular Microbiology 11(5): 811-818 (1994).

(Continued)

*Primary Examiner*—Nashaat T. Nashed
(74) *Attorney, Agent, or Firm*—Finnegan, Henderson, Farabow, Garrett & Dunner, L.L.P.

(57) ABSTRACT

The present invention relates to an esterase, its DNA, its overexpression and a method for preparing an optically active aryl propionic acid of formula (1) using the same in high yield,

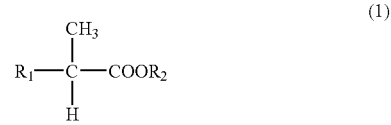

wherein $R_1$ represents an aryl group; and $R_2$ represents a hydrogen atom.

6 Claims, 6 Drawing Sheets

U.S. PATENT DOCUMENTS 6,201,151 B1    3/2001    Tsai et al. ................... 562/489
6,255,347 B1    7/2001    Xiaotao et al. ............. 514/570

FOREIGN PATENT DOCUMENTS

KR    1999-0042314    6/1999
KR    2000-0002565    1/2000
KR    2001-0044879    6/2001

OTHER PUBLICATIONS

Kim et al., Cloning of *Pseudomonas fluorescens* carboxylesterase gene and characterization of its product in *Escherichia coli*, Biosci. Biotech. Biochem. 58(1):111-116 (1994).

McKay et al., Molecular analysis of an esterase-encoding gene from lipolytic psychotrophic pseudomonad, J. General Microbiology 138:701-708 (1992).

Lane 1 : protein molecular weight marker
Lane 2 : total cellular fraction (37°C)
Lane 3 : total cellular fraction (37°C)
Lane 4 : soluble fraction (37°C)
Lane 5 : insoluble fraction (37°C)
Lane 6 : total cellular fraction (20°C)
Lane 7 : total cellular fraction (20°C)
Lane 8 : soluble fraction (20°C)
Lane 9 : insoluble fraction (20°C)

Lane 1 : protein molecular size marker
Lane 2 : total cellular fraction (20°C)
Lane 3 : fraction from ion exchange chromatography Lane 1 : protein molecular size marker
Lane 2 : fraction from ion exchange chromatography
Lane 3 : fraction from gel chromatography

SEQUENCE LISTING

```
<160> NUMBER OF SEQ ID NOS: 8

<210> SEQ ID NO 1
<211> LENGTH: 1143
<212> TYPE: DNA
<213> ORGANISM: Pseudomonas sp. BHY-1(KCTC 0688BP)

<400> SEQUENCE: 1
gtgcagattc agggacatta cgagcttcaa ttcgaagcgg tgcgcgaagc tttcgccgca      60
ctgttcgacg atccccagga acgcggcgcc gcgttgtgca tccgggtcgg cggggaaacc     120
gtcctcgacc tctggtccgg caccgccgac aaggacggcg ccgaggcctg gcacagcgac     180
accatcgcca acctgttctc ctgcaccaag accttcaccg ccgtcaccgc gctgcaactg     240
gttgccgaag gcaaattgca gctcgatgcg ccggtcgccc gttactggcc ggaattcgcc     300
gccgccggca aggaatccgt aaccctgcgc caactgcttt gccatcaggc cggtctgccg     360
gccctgcgcg aattgctggc gccggaagcg ctgtatgact ggcaaaccat ggtcgacgcc     420
ctcgcggccg aagcaccgtg gtggackccg ggcaccggty atkgctatgc cgcgatcacc     480
tacggctggc tgattggcga attgctgcgg cgtgccgacg gtcgcgggcc gggggaatcg     540
atcgtggcgc gggtcgccaa accgctgggg ctggatttcc atgtcggtct ggccgacgag     600
gaattccatc gcgtggcgca catcgcccgg ggcaagggca acaccggcga cgccgcttcc     660
cagcgcctgc tgcaagtgac catgcgcgag ccgacggcca tgaccacccg ggccttcacc     720
aatcccccgt cggtgctcac cagcaccaac aagccggagt ggcgccgcat gcagcaaccg     780
gcagccaacg gccacggcaa tgcacgcagc ctggccgggt tttacgccgg tctgctcgac     840
ggcagcctgc tggaaagcga aatgctcgaa gaactgaccc gcgaacacag cctcggcgag     900
gacaagacct tgctgacccg cacccgtttc ggtctcggtt gcatgctcga tcaacccgac     960
gtgccgaacg ccacttacgg cctcggcccg cgtgcattcg gccatccggg tgcgggcggt    1020
```

```
tccatcggtt ttgctgatcc ggagcacgat gtggccttcg gatttgtgac aaatacccctg    1080 gggccgtacg tcttgatgga tccgcgcgcg cagaagctgg cgcgggtact agccacttgt    1140
ctg                                                                   1143
```

<210> SEQ ID NO 2
<211> LENGTH: 381
<212> TYPE: PRT
<213> ORGANISM: Pseudomonas sp. BHY-1(KCTC 0688BP)

<400> SEQUENCE: 2

```
Val Gln Ile Gln Gly His Tyr Glu Leu Gln Phe Glu Ala Val Arg Glu
 1               5                  10                  15

Ala Phe Ala Ala Leu Phe Asp Asp Pro Gln Glu Arg Gly Ala Ala Leu
            20                  25                  30

Cys Ile Arg Val Gly Gly Glu Thr Val Leu Asp Leu Trp Ser Gly Thr
        35                  40                  45

Ala Asp Lys Asp Gly Ala Glu Ala Trp His Ser Asp Thr Ile Ala Asn
    50                  55                  60

Leu Phe Ser Cys Thr Lys Thr Phe Thr Ala Val Thr Ala Leu Gln Leu
65                  70                  75                  80

Val Ala Glu Gly Lys Leu Gln Leu Asp Ala Pro Val Ala Arg Tyr Trp
                85                  90                  95

Pro Glu Phe Ala Ala Ala Gly Lys Glu Ser Val Thr Leu Arg Gln Leu
            100                 105                 110

Leu Cys His Gln Ala Gly Leu Pro Ala Leu Arg Glu Leu Leu Ala Pro
        115                 120                 125

Glu Ala Leu Tyr Asp Trp Gln Thr Met Val Asp Ala Leu Ala Ala Glu
    130                 135                 140

Ala Pro Trp Trp Thr Pro Gly Thr Gly His Gly Tyr Ala Ala Ile Thr
145                 150                 155                 160

Tyr Gly Trp Leu Ile Gly Glu Leu Leu Arg Arg Ala Asp Gly Arg Gly
                165                 170                 175

Pro Gly Glu Ser Ile Val Ala Arg Val Ala Lys Pro Leu Gly Leu Asp
            180                 185                 190

Phe His Val Gly Leu Ala Asp Glu Glu Phe His Arg Val Ala His Ile
        195                 200                 205

Ala Arg Gly Lys Gly Asn Thr Gly Asp Ala Ala Ser Gln Arg Leu Leu
    210                 215                 220

Gln Val Thr Met Arg Glu Pro Thr Ala Met Thr Thr Arg Ala Phe Thr
225                 230                 235                 240

Asn Pro Pro Ser Val Leu Thr Ser Thr Asn Lys Pro Glu Trp Arg Arg
                245                 250                 255

Met Gln Gln Pro Ala Ala Asn Gly His Gly Asn Ala Arg Ser Leu Ala
            260                 265                 270

Gly Phe Tyr Ala Gly Leu Leu Asp Gly Ser Leu Leu Glu Ser Glu Met
        275                 280                 285

Leu Glu Glu Leu Thr Arg Glu His Ser Leu Gly Glu Asp Lys Thr Leu
    290                 295                 300

Leu Thr Arg Thr Arg Phe Gly Leu Gly Cys Met Leu Asp Gln Pro Asp
305                 310                 315                 320

Val Pro Asn Ala Thr Tyr Gly Leu Gly Pro Arg Ala Phe Gly His Pro
                325                 330                 335

Gly Ala Gly Gly Ser Ile Gly Phe Ala Asp Pro Glu His Asp Val Ala
```

```
               340             345             350
Phe Gly Phe Val Thr Asn Thr Leu Gly Pro Tyr Val Leu Met Asp Pro
        355                 360                 365
Arg Ala Gln Lys Leu Ala Arg Val Leu Ala Thr Cys Leu
    370                 375                 380

<210> SEQ ID NO 3
<211> LENGTH: 45
<212> TYPE: DNA
<213> ORGANISM: Artificial Sequence
<220> FEATURE:
<223> OTHER INFORMATION: Description of Artificial Sequence: N-Terminal
      primer

<400> SEQUENCE: 3
gggaatttcc atatgcagat tcagggacat tacgagcttc aattc             45

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence:  C-terminal
      primer

<400> SEQUENCE: 4
ccgctcgagt tacagacaag tggctagtac ccgcgccag                    39

<210> SEQ ID NO 5
<211> LENGTH: 57
<212> TYPE: DNA
<213> ORGANISM: Artificial Sequence
<220> FEATURE:
<223> OTHER INFORMATION: Description of Artificial Sequence:  N-terminal
      primer

<400> SEQUENCE: 5
gggaatttcc atatgcacca ccaccaccac caccaaattt tcgtcaaaac tctaaca    57

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:  C-terminal
      primer

<400> SEQUENCE: 6
accacccctc aacctcaaga c                                       21

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence:  N-terminal
      primer

<400> SEQUENCE: 7
cagattcagg gacattacga gcttcaattc                              30

<210> SEQ ID NO 8
<211> LENGTH: 39
<212> TYPE: DNA
<213> ORGANISM: Artificial Sequence
<220> FEATURE:
```

-continued

```
<223> OTHER INFORMATION: Description of Artificial Sequence:  N-terminal
      primer

<400> SEQUENCE: 8
ccggaattcc agattcaggg acattacgag cttcaattc                          39
```

ESTERASE, ITS DNA, ITS OVEREXPRESSION AND PRODUCTION OF OPTICALLY ACTIVE ARYL PROPIONIC ACIDS USING THE SAME

This application is a continuation-in-part of application Ser. No. 10/118,047, currently now abandoned, as originally filed on Apr. 9, 2002, and incorporated herein by reference.

FIELD OF THE INVENTION

The present invention relates to an esterase, its DNA, its overexpression and a method for preparing optically active aryl propionic acids using the same in high yield. More particularly, the present invention relates to an esterase having a stereoselective hydrolyase activity, its manufacturing method for mass production by using recombinant *E. coli* expression system and a method for preparing optically active aryl propionic acids expressed by the following formula (1) using the same,

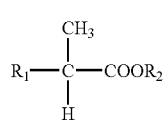
(1)

wherein $R_1$ represents an aryl group; and $R_2$ represents a hydrogen atom.

BACKGROUND OF THE INVENTION

Indeed, FDA (Food and Drug Administration)'s Policy Statement for Development of New Drugs recommends "that the pharmacokinetic profile of each isomer should be characterized in animals and later compared to the clinical pharmacokinetic profile obtained in Phase I" drug testing. Thus, the demand for racemic switch technologies to produce each pure isomer has been rapidly increased in recent years.

Aryl propionic acids are non-steroidal anti-inflammatory drugs and known as profen drugs such as ibuprofen, ketoprofen, naproxen, flurbiprofen, fenoprofen, suprofen and the like. It is generally believed that (S)-profens have higher pharmacological effects of the racemic mixture of profens bearing at least one benzene ring. A method for preparing optically pure (S)-profen drugs involves the conversion of a racemic mixture of profen ester to optically active profen carboxylic acid by reacting with a stereoselective chiral enzyme.

However, it has been recently reported that (R)-enantiomers of profens also exhibit therapeutic effects. Particularly, U.S. Pat. No. 6,255,347 discloses that (R)-enantiomer of ibuprofen may be used as a prophylactic and therapeutic agent in the treatment of diseases such as cancers, Alzheimer's and Alzheimer's-related diseases. In the method for preparing (R)-enantiomer of aryl propionic acid, a racemic mixture of aryl propionic acid is treated with an esterase to produce an ester of (S)-enantiomer of aryl propionic acid and un-reacted (R)-enantiomer of aryl propionic acid is recovered.

Further, inventors of the present invention have identified the presence of a stereoselective hydrolase activity in *Pseudomonas* sp. and its use in the preparation of (S)-profen (KR Patent Application No. 2000-02565). U.S. Pat. No. 6,201,151 discloses a process for preparing an optically active (S)-aryl propionic acid by hydrolyzing racemic thioester of aryl propionic acid in the presence of a (S)-stereoselective lipase. KR Patent Application No. 2001-0044879 discloses a process for preparing optically pure acetylmercaptoisobutylate using an esterase isolated from *Pseudomonas aeruginosa*. KR Patent Application No. 1996-14399 discloses a process for preparing optically pure aryl carboxylic acid stereoselectively from a racemic mixture of α-aryl carboxylic acid using S-(-)-α-ethyl benzylamine. KR Patent Application No. 1999-0042314 discloses a process for preparing optically active carboxylic acids and esters as drugs for the treatment of hypertension using a hydrolase isolated from *Klebsiella pneumoniae*. U.S. Pat. No. 5,516,690 discloses that (S)-ketoprofen can be produced with a purity greater than 95% using isolated *Trichosporon laibacchii*.

However, the above-mentioned enzymes were not shown suitable for the selective production of optically pure (S)- or (R)-enantiomers of aryl propionic acid and there has been no report on mass production of those enzymes.

SUMMARY OF THE INVENTION

Accordingly, an object of the present invention is to provide an esterase having excellent stereoselectivity and its DNA sequence.

Another object of the present invention is to provide a method for producing the esterase in a mass production scale by overexpression of the esterase in recombinant *E. coli*.

Further object of the present invention is to provide a process for preparing optically pure aryl propionic acid in high yield using the esterase,

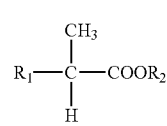
(1)

wherein $R_1$ represents an aryl group; and $R_2$ represents a hydrogen atom.

BRIEF DESCRIPTION OF THE DRAWINGS

The above and other objects and features of the present invention will become apparent from the following description of the invention, when taken in conjunction with the accompanying drawings, in which.

DETAILED DESCRIPTION OF THE PREFERRED EMBODIMENTS

Figure 1:
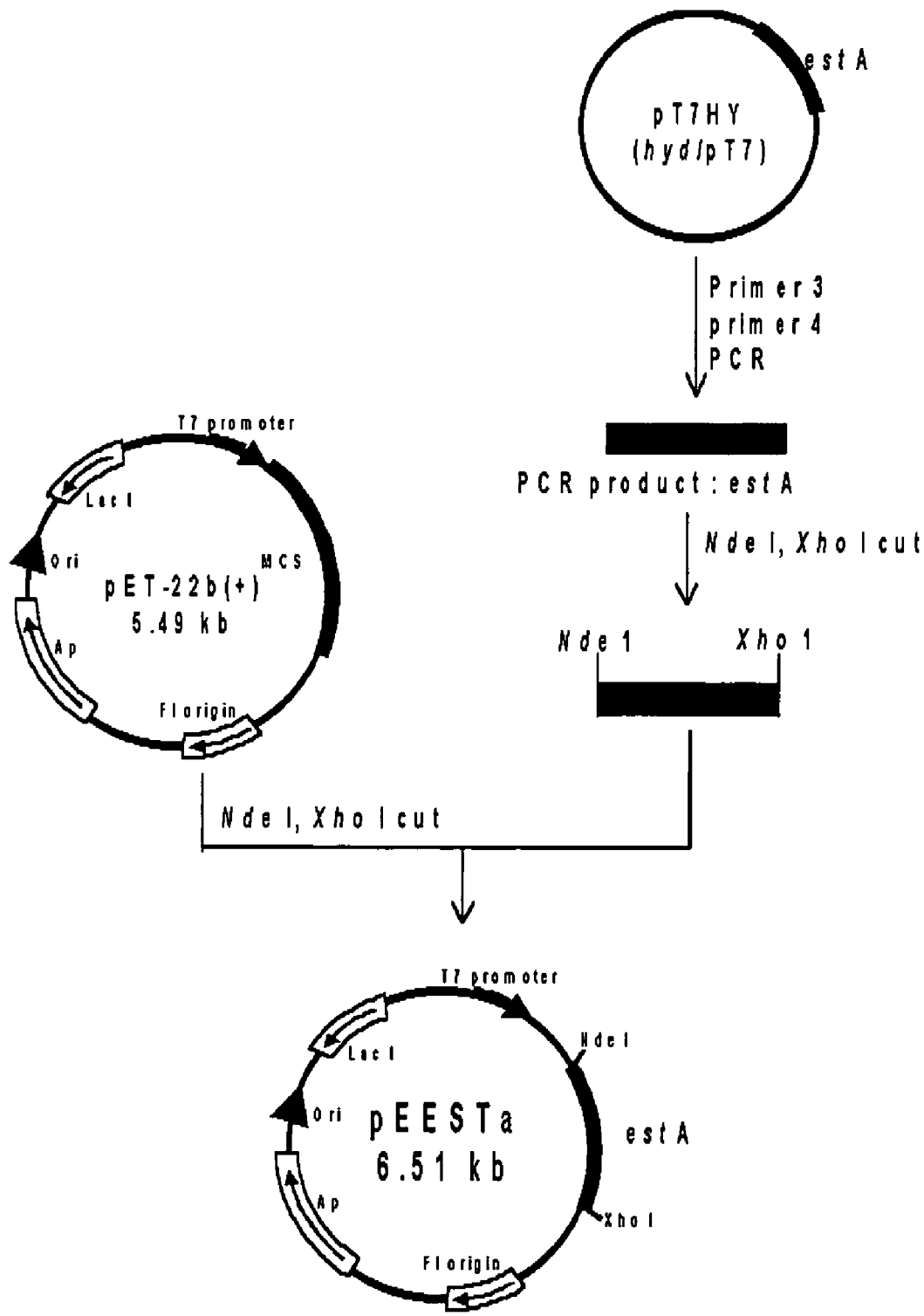
FIG. 1 represents a manufacturing process of an esterase expression vector, pEESTa.

The present invention relates to an esterase having excellent stereoselectivity, its DNA and its mass production by transformation thereof. In accordance with one aspect of the invention, there is provided a method for preparing optically pure aryl propionic acid of formula (1) using the same esterase,

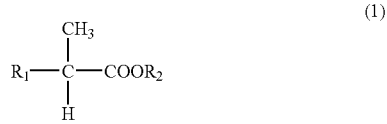

(1)

wherein $R_1$ represents an aryl group; and $R_2$ represents a hydrogen atom.

The present invention is described in detail as set forth hereunder. The esterase of the present invention is identified by the SEQ. ID. NO: 1 for its gene and the SEQ. ID. NO: 2 for its amino acid sequence and has a molecular weight of 41 kDa.

Further, the esterase derived from *Pseudomonas* sp. BHY-1 hydrolyzes racemic ester of a carboxylic acid unsymmetrically to produce the corresponding optically pure carboxylic acid. On the other hand, *Pseudomonas* sp. BHY-1 has a stereoselective hydrolase activity to convert racemic ester of aryl propionic acid to one-enantiomer aryl propionic acid. The racemic ester of aryl propionic acid used as a substrate may be prepared from racemic profen by a conventional method. Examples of the profen include ketoprofen, ibuprofen, naproxen, flurbiprofen, fenoprofen, suprofen and the like.

The inventors of the invention have selected *Pseudomonas* sp. BHY-1 exhibiting excellent stereoselectivity from soil and analyzed gene sequence of the esterase to obtain optically pure aryl propionic acid. Further, the present invention provides a construction of a recombinant *E. coli* expression vector to produce the esterase in an industrial scale. A novel esterase expression vector named as a pEESTa is constructed by introducing an NdeI restriction site to the N-terminal of the esterase and an XhoI restriction site to the C-terminal, performing PCR (Polymerase chain reaction) to amplify DNA fragments, and incorporating a T7 promoter and a T7 terminator. Other pEUbiESTa and pETrx-ESTa vectors are also constructed by introducing ubiquitin and thioredoxin to improve production efficiency. These vectors are also incorporated with T7 promoter and T7 terminator and produce an active esterase more effectively. Theses expression vectors are then transformed into *E. coli* to produce *E. coli* transformants BL21(DE3)/pEESTa, BL21/pEUbiESTa, and BL21/pETrxESTa.

Thus obtained *E. coli* transformants BL21(DE3)/pEESTta are cultured and the cultured *E. coli* is then recovered. Examples of the profens used as a substrate to identify an activity of the obtained recombinant esterase include ethyl esters of ibuprofen, ketoprofen, naproxen, and flurbiprofen. As a result, an enantiomeric excess ($ee_p$) of (S)-enantiomer profen produced by using the recombinant esterase of the present invention is not lower than 98%. It is preferable to maintain the pH in the range of from 6.0 to 12.0, more preferably from 8.0 to 10.0 and a temperature of from 15 to 80° C., more preferably 30 to 80° C. during resolution of aryl carboxylic acids. Thus obtained recombinant esterase may be purified by ion exchange chromatography, metal affinity chromatography or gel chromatography.

This invention is explained in greater detail based on the following Examples but they should not be construed as limiting the scope of this invention.

PREPARATION EXAMPLE

Preparation of Racemic Profen Ethyl Ester

Racemic profen (30 g) and ethanol (100 mL) were mixed and reacted in the presence of hydrosulfuric acid (2.5 mL) at 90° C. for 5 hours. The unreacted ethanol was removed by evaporation under the pressure. The reaction mixture was extracted with 1 M sodium bicarbonate solution three times to obtain racemic profen ethyl ester.

$$\text{Conversion (\%)} = \frac{\text{Conc. of (S)-arylpropionic acid} + \text{Conc. of (R)-arylpropionic acid}}{\text{Conc. of arylpropionic ester}} \times 100 \quad \text{Equation 1}$$

$$\text{Enantiomeric excess (\%)} = \frac{\text{Conc. of (S)-arylpropionic acid} - \text{Conc. of (R)-arylpropionic acid}}{\text{Conc. of (S)-arylpropionic acid} + \text{Conc. of (R)-arylpropionic acid}} \times 100 \quad \text{Equation 2}$$

Example 1

Sequence Analysis of a Novel Esterase Gene

Chromosomal DNA isolated from *Pseudomonas* sp. BHY-1 was partially digested with Sau3A, ligated with BamHI-digested pUC119 vector and then was transformed into *E. coli* DH5α. One of the clones, carrying a plasmid named as pT7HY (about 3 kb), exhibited enzymatic activity producing (S)-ketoprofen from (R, S)-ketoprofen ester and was chosen for further study. And also, the results showed that the novel esterase gene has a molecular weight of about 41 kDa. Transformants were selected based on a tributyrin hydrolysis as well as a stereoselectivity towards ketoprofen ester. The results showed that the novel esterase gene has a molecular weight of about 41 kDa and consists of 1,143 bp nucleotides (381 amino acids). The gene was registered in Genbank of NCBI and was assigned the Reg. No. AF380303 but has not been published yet. The novel esterase is identified by the SEQ. ID. NO: 1 for its gene and the SEQ. ID. NO: 2 for its amino acid sequence.

Example 2

Construction of an Expression Vector for a Novel Esterase Gene

Chromosomal DNA isolated from *Pseudomonas* sp. BHY-1 was partially digested with Sau3A, ligated with BamHI-digested pUC119 vector and then transformed into *E. coli* DH5α. One of the clones, carrying a plasmid named as pT7HY (about 3 kb), exhibited enzymatic activity producing (S)-ketoprofen from (R, S)-ketoprofen ester. The novel estererase cDNA coding sequence was amplified by PCR using pT7HY as a template. The primers used in the above PCR are as follows.

N-terminal primer                [SEQ. ID. NO: 3]
5'-GGG AAT TTC CAT ATG CAG ATT
CAG GGA CAT TAC GAG CTT CAA TTC-3'

C-terminal primer                [SEQ. ID. NO: 4]
5'-CCG CTC GAG TTA CAG ACA AGT GGC
TAG TAC CCG CGC CAG-3'

The N-terminal primer was introduced with an NdeI restriction site and also ATG was introduced as an initiation codon in place of GTG, whereas the C-terminal primer was introduced with an XhoI restriction site. The product with a size of about 1,100 bp obtained from the above PCR was double-digested with NdeI and XhoI and then separated on an agarose gel. The novel esterase gene fragment isolated from the above agarose gel was ligated into a 5,400 bp DNA fragment of pET22b (Novagen Co., Ltd., U.S.), an *E. coli* expression vector, double-digested with NdeI and XhoI by using a ligase. Then, an expression vector was constructed so that the novel esterase gene can be expressed, wherein its gene translation is carried out by T7 promoter and T7 terminator, and was named as pEESTa (FIG. 1). The vector pEESTa was then transformed into *E. coli* BL21(DE3) according to Simanis. Thus transformed *E. coli* BL21(DE3)/pEESTa was deposited to the Genebank of KRIBB on Nov. 20, 2001 and assigned the Accession No. KCTC 10122BP.

Example 3

Expression of a Novel Esterase Gene

Figure 4:
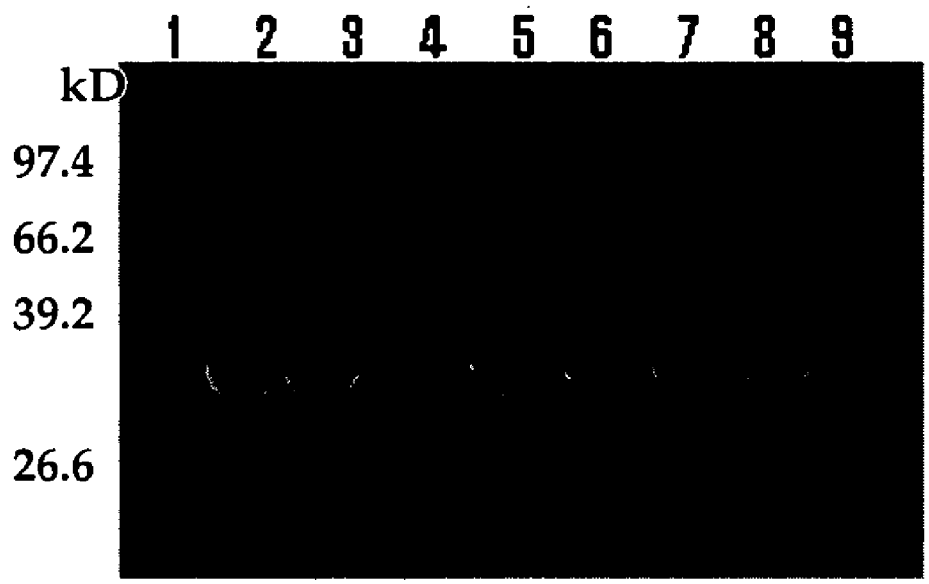
FIG. 4 represents an acryl amide gel electrophoresis of an esterase expression.

The above *E. coli* transformant BL21(DE3)/pEESTa (KCTC 10122BP) was cultured in a solid LB medium (yeast extract 0.5%, tryptone 1%, and NaCl 1%). Thus cultured *E. coli* was inoculated into a liquid LB medium containing ampicillin (50 μg/mL), and then re-cultured at 37° C. until the $OD_{600}$ reached 0.6. Then, the culture was added with isopropylthio-β-D-galactoside (IPTG) to the final concentration of 1 mM and cultured further for 4 hr for the expression of an esterase gene. Cold shock response was employed for the production of an active esterase because an esterase becomes in the form of an insoluble inclusion body, which has little enzyme activity, when *E. coli* transformant BL21(DE3)/pEESTa (KCTC 10122BP) is produced by culturing at 37° C. (FIG. 4). Cold shock response is a method to produce an active enzyme wherein a given culture is incubated at 37° C. until the expression is induced by IPTG followed by lowering the culturing temperature to 5–25° C. (Pamela G. Jones & Masayori Inouye, The cold-shock response, *Mol. Microbiol.*, 11, 5, 1994).

Example 4

Construction of an Expression Vector for a Novel Ubiquitin-fused Esterase Gene

A 228 bp fragment encoding ubiquitin (76 amino acids) was amplified by PCR using *Saccharomyces cerevisiae* genomic DNA as a template. The primers used in the PCR are as follows.

N-terminal primer                [SEQ. ID. NO: 5]
5'-GGG AAT TTC CAT ATG CAC CAC CAC
CAC CAC CAC CAA ATT TTC GTC AAA ACT CTA ACA-3'

C-terminal primer                [SEQ. ID. NO: 6]
5'-ACC ACC CCT CAA CCT CAA GAC-3'

The N-terminal primer was introduced with an NdeI restriction site while the C-terminal primer, where a novel esterase is to be ligated, was treated to be blunt-ended. The product (fragment 1: 228 bp) obtained from the above PCR was digested with NdeI and then separated on an agarose gel.

The coding region of novel esterase was isolated by PCR. The primers used in the above PCR are as follows.

N-terminal primer                [SEQ. ID. NO: 7]
5'-CAG ATT CAG GGA CAT TAC GAG CTT CAA TTC-3'

C-terminal primer                [SEQ. ID. NO: 4]
5'-CCG CTC GAG TTA CAG ACA AGT GGC TAG TAC CCG-3'

The N-terminal primer was treated to be blunt-ended so that it can be ligated to ubiquitin sequence and then introduced with an XhoI restriction site. The product (fragment 2: 1,100 bp) obtained from the above PCR was digested with XhoI and then separated on an agarose gel.

Figure 2:
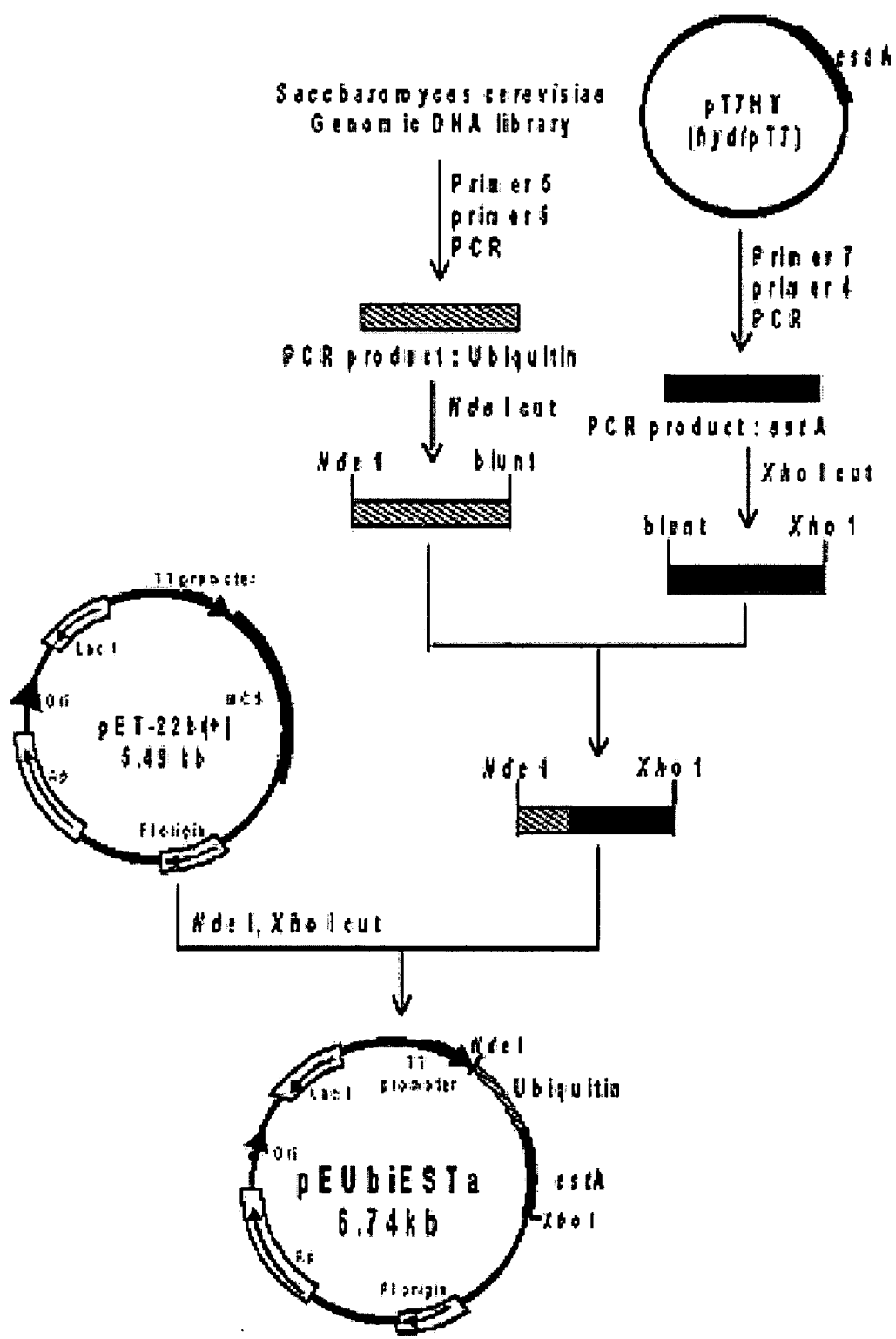
FIG. 2 represents a manufacturing process of an esterase expression vector, pEUbiESTa.

The novel esterase gene fragment as well as the ubiquitin gene fragment (PCR-amplified product) isolated from the above agarose gels were ligated into a 5,400 bp DNA fragment of pET22b (Novagen Co., Ltd., U.S.), which was digested with NdeI and XhoI by using a ligase. Then, an expression vector was constructed so that an esterase can be expressed, wherein its gene translation is carried out by a T7 promoter and a T7 terminator, and was named as pEUbi-ESTa (FIG. 2).

Example 5

Construction of an Expression Vector for a Novel Thioredoxine-fused Esterase Gene In order to increase the rate of production and expression of the novel esterase having an activity, an expression vector introduced with thioredoxine was constructed. The novel estererase cDNA coding sequence was amplified by PCR using pT7HY as a template. The primers used in the above PCR are as follows.

N-terminal primer                [SEQ. ID. NO: 8]
5'-CCG GAA TTC CAG ATT CAG GGA CAT
TAC GAG CTT CAA TTC-3'

C-terminal primer                [SEQ. ID. NO: 4]
5'-CCG CTC GAG TTA CAG ACA AGT GGC TAG TAC CCG-3'

N-terminal of primers were treated with EcoRI so that they can be ligated to thioredoxine sequences and then introduced with an XhoI restriction site. The PCR product (1,100 bp) was gel purified and digested with EcoRI and Xho.

Figure 3:
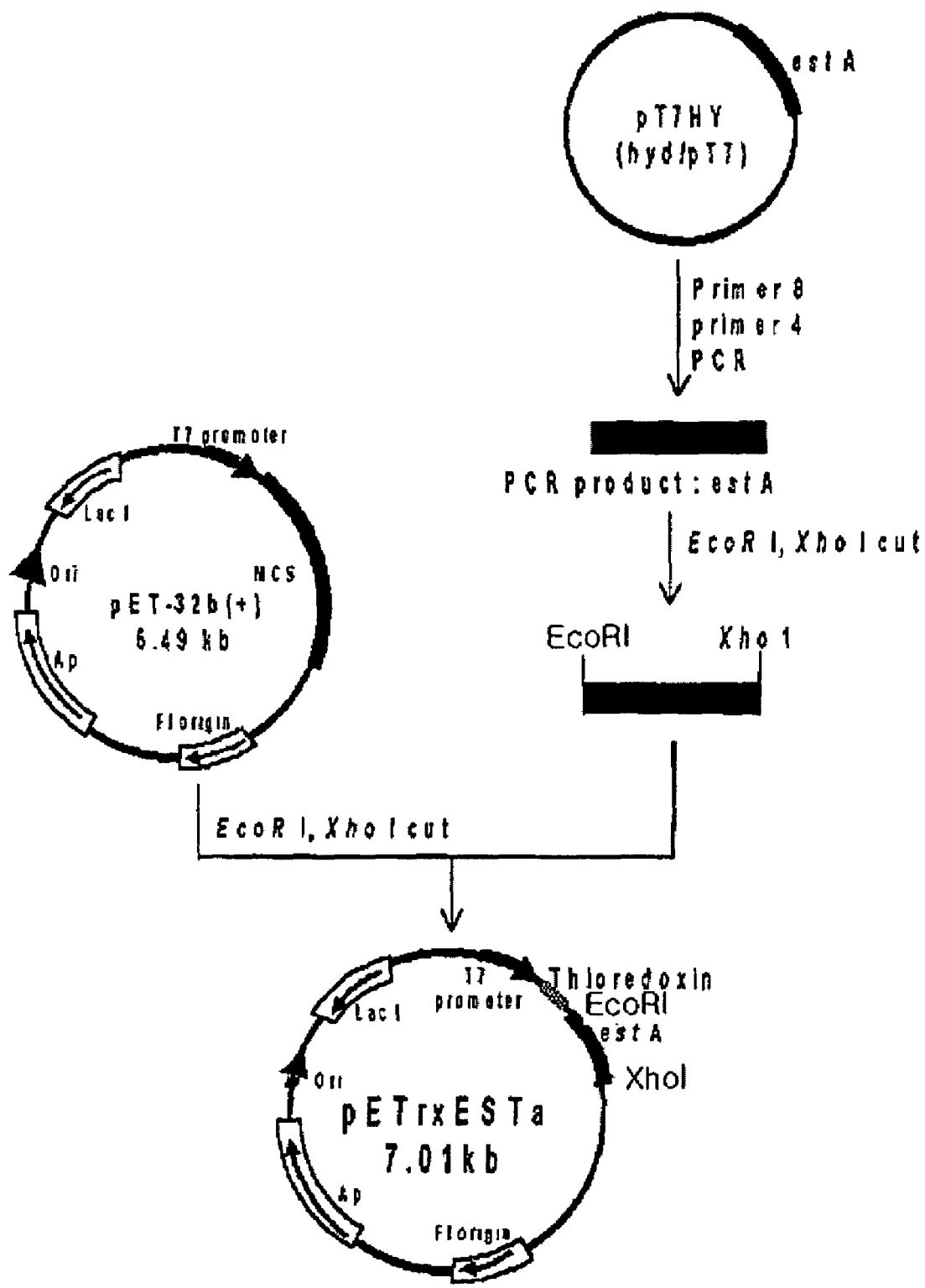
FIG. 3 represents a manufacturing process of an esterase expression vector, pErxESTa.

The novel esterase gene fragment isolated from the above agarose gel was ligated into a 5,900 bp DNA fragment of pET32b (Novagen Co., Ltd., U.S.), an *E. coil* expression vector that contains thioredoxine which was double-digested with EcoRI and XhoI, by using a ligase. Then, an expression vector was constructed so that the esterase can be expressed, wherein its gene translation is carried out by a T7 promoter and a T7 terminator, and was named as pETrxESTa (FIG. 3). The two fusion partners have six histidine tags and are thus easily purified and are also characterized in that they have special cleavage sites for ubiquitin hydrolase and enterokinase (FIGS. 2 and 3).

Example 6

Expression of an Esterase

The above *E. coli* transformant BL21(DE3)/pEESTa (KCTC 10122BP) was inoculated into an LB medium and cultured at 37° C. until the $OD_{600}$ reached 0.6. Then, the culture was added with IPTG to the final concentration of 1 mM and cultured further for 4 hr to induce the expression of the fused esterase gene. The expressed fused esterase was identified on an SDS-PAGE gel (12% acrylamide) (see Example 3) and compared with the esterase in the Example 3 (FIG. 4). Cold shock response was employed for the production of an active esterase because an esterase becomes in the form of an insoluble inclusion body, which has little enzymatic activity, when *E. coli* transformant BL21(DE3)/pEESTa (KCTC 10122BP) is produced by culturing at 37° C. (FIG. 4). It is noteworthy that the culture is incubated at 37° C. until the expression is induced by IPTG followed by lowering the culturing temperature to 20° C., whereby the esterase is produced in an active form. The result showed that the above two fused proteins of ubiquitin-esterase and thioredoxine-esterase, which were both produced by cold shock response, were shown to retain their optical selectivity and hydration capability.

Example 7

Identification of a Novel Esterase Expression

The culture was centrifuged for 20 min at 7,000 rpm and the cells were recovered. To study the expression level of the esterase that is expressed, the whole cells were divided into a soluble fraction and an insoluble fraction via sonication and its expression was examined. Three samples such as a whole fraction, a soluble fraction and an insoluble fraction, was dissolved in 100 µL of protein solubilizing buffer solution (12 mM Tris-HCl pH 6.8, 5% glycerol, 2.88 mM mercaptoethanol, 0.4% SDS, 0.02% bromophenol blue) and then heated for 5 min at 100° C. Ten µL each of thus formed solutions was loaded onto a polyacrylamide gel, wherein a 0.75 mm thick 12% gradient separating gel (pH 8.8, 20 cm(W)×10 cm(H)) was covered with a 5% stacking gel (pH 6.8, 10 cm(W)×12 cm(H)). Then, electrophoresis was performed for 80 min (120 V, 60 mA) and the gel was stained with Coomassie Blue. The gel scanning (BioRad, Imaging Densitometer GS-700, U.S.) result of the esterase revealed that the expression level after IPTG induction was 46.7%, and 94.2% of the total expression was present in the form of an insoluble inclusion body.

Example 8

Purification of a Novel Esterase Via Anion Exchange Chromatography

Figure 5:
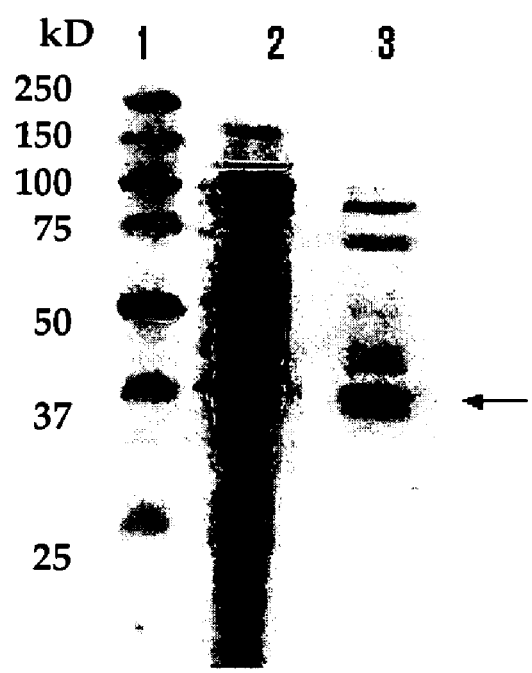
FIG. 5 represents an acryl amide gel electrophoresis of an esterase purified via anion exchange chromatography.

Ion exchange chromatography was performed to purify the novel esterase produced from the recombinant *E. coli*. The chromatography was performed by using Q-Sepharose (Pharmacia Co., Ltd., Sweden) as a resin at pH 8.5 at the rate of 4.0 mL/min. Samples were prepared by crushing cell walls of *E. coli* by using a sonicator followed by filtering thus obtaining a soluble fraction through micro filter (0.2 µm). Q-Sepharose was equilibrated with 50 mM Tris-HCl (pH 8.5) buffer solution. The esterase was fractioned by using NaCl linear gradient of an eluent buffer solution (1N NaCl/50 mM Tris-HCl, pH 8.5) wherein the sample was first put into the chromatography column followed by a thorough rinse with an equilibrium buffer solution. Thus purified esterase was identified on an SDS-PAGE gel electrophoresis as in the Example 6 (FIG. 5).

Example 9

Purification of a Novel Esterase Via Gel Chromatography

Figure 6:
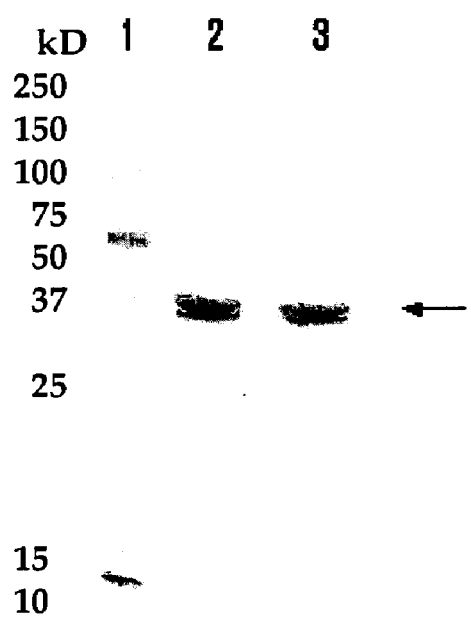
FIG. 6 represents an acryl amide gel electrophoresis of an esterase purified via gel chromatography.

Gel chromatography was performed by using the fraction obtained from the above anion exchange chromatography. The chromatography was performed by using Sephacry S-200-HR (Pharmacia Co., Ltd., Sweden) as a resin at pH 8.5 at the rate of 0.3 mL/min. Samples were prepared by filtering the fraction obtained from the ion exchange chromatography through micro filter (0.21 µm). Sephacry S-200-HR was equilibrated with 50 mM Tris-Cl/10 mM NaCl buffer solution. The esterase was fractioned after putting the sample into the chromatography column and flowing it at the rate of 0.3 mL/min. Thus purified esterase was identified on an SDS-PAGE gel as in the Example 6(FIG. 6).

Example 10

Effect of Optical Resolution Conditions on Optical Resolution of a Novel Esterase 1. Effect of pH The hydration by a novel esterase is mostly performed in a buffered solution and thus the structure of the enzyme can be influenced much by the pH and chemical properties of a buffer solution being used. When using *Pseudomonas* sp. BHY-1 as a whole cell enzyme, the optimal enzyme activity was observed at pH 8.5. In the case of the novel esterase, the enzyme activity was shown to have a relatively wide pH range of 7–11 and the optical selectivity was shown to be optimal at pH 10.0 as shown in the following Table 1.

TABLE 1

| | Optimal pH of Esterase | | | | | |
|---|---|---|---|---|---|---|
| | PH | | | | | |
| | 7.0 | 8.0 | 8.5 | 9.0 | 10.0 | 11.0 |
| Conversion (%) | 1.8 | 2.4 | 2.0 | 2.2 | 7.9 | 5.4 |
| Enantiomeric excess (%) | 100 | 100 | 100 | 100 | 100 | 41 |

2. Effect of Temperature

Optimal temperature for optical resolution is affected by the fictive temperature, defined as racemic temperature, and the optical selectivity in response to a temperature increase tends to vary depending on the kind of an enzyme. The novel esterase of the present invention is shown to have an excellent optical selectivity and the following shows the reaction rate of the enzyme. The reaction rate was observed at 10° C.–90° C., a temperature range for culturing *Pseudomonas* sp. BHY-1, and the optimal reaction rate was observed at 60° C.

TABLE 2

Optimal temperature of Esterase

| | Temperature (° C.) | | | | | | |
|---|---|---|---|---|---|---|---|
| | 30 | 40 | 50 | 60 | 70 | 80 | 90 |
| Conversion (%) | 7.9 | 8.9 | 11.5 | 13.1 | 12.8 | 10.9 | 9.9 |
| Enantiomeric excess (%) | 100 | 100 | 100 | 100 | 100 | 41 | 41 |

3. Type of Reaction Substrates

Reaction substrates are in the form of ester and are mostly water insoluble. Therefore, it becomes necessary to mediate the reaction substrate to bind the enzyme for a desired enzyme reaction. In general, organic solvents such as dimethylsulfoxide, dimethylformamide, tetrahydrofuran, cyclohexane, benzene, etc., or a non-ionic surfactant are used to serve the above mediation purpose. It is important to determine an organic solvent or a surfactant suitable for a given substrate. In profen pharmaceuticals, for example, Triton X-100 and dimethylsulfoxide were shown most effective.

Example 11

Optical Resolution of Aryl Propionic Acid by Using a Novel Recombinant Esterase Hydration was performed using 20 mM esters of ibuprofen, ketoprofen, and flurbiprofen to produce optically active ibuprofen, ketoprofen, and flurbiprofen. The reaction was performed at 37° C. (pH 8.5) with a reaction volume of 500 µL. Twenty four hours after the enzyme reaction, there was about 40% of conversion and enantiomeric excess ($ee_p$) was higher than 98.5% of optical selectivity as shown in the following Table 3.

TABLE 3

| Substrate | Conversion (%) | Enantiomeric excess (%) |
|---|---|---|
| Ibuprofen | 40.9 | >99 |
| Ketoprofen | 39.3 | >99 |
| Flurbiprofen | 41.4 | 99 |

The novel esterase of the present invention derived from *Pseudomonas* sp. BHY-1 can be used in producing optically pure (S)- or (R)-type of aryl propionic acid having a pharmaceutical activity with high efficiency from racemic aryl propionic acid.

---

What is claimed is:

1. An isolated esterase gene identified by SEQ. ID. NO:1.

2. An expression vector containing the esterase gene in claim 1.

3. The expression vector according to claim 2, wherein said expression vector is pEESTa, pEUbiESTa or pETrxESTa.

4. An isolated cell culture transformed by the expression vector in claim 2.

5. The cell culture according to claim 4, wherein said cell culture is *E. coli* BL21(DE3)/pEESTa, L21/pEUbiESTa, or BL21/pETrxESTa.

6. A method for preparing an esterase for mass production by isolation and purification of expressed esterase from the transformed cell culture in claim 4.

* * * * *